United States Patent
Fu et al.

(10) Patent No.: US 7,831,073 B2
(45) Date of Patent: Nov. 9, 2010

(54) PRECISION REGISTRATION OF X-RAY IMAGES TO CONE-BEAM CT SCAN FOR IMAGE-GUIDED RADIATION TREATMENT

(75) Inventors: Dongshan Fu, Santa Clara, CA (US); Michael J. Saracen, Oakland, CA (US); Gopinath Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 582 days.

(21) Appl. No.: 11/171,842

(22) Filed: Jun. 29, 2005

(65) Prior Publication Data

US 2007/0003123 A1   Jan. 4, 2007

(51) Int. Cl.
*G06K 9/00* (2006.01)

(52) U.S. Cl. ........... 382/128; 600/300

(58) Field of Classification Search ......... 382/128–132; 600/300
See application file for complete search history.

(56) References Cited

U.S. PATENT DOCUMENTS

| | | | |
|---|---|---|---|
| 4,791,934 A * | 12/1988 | Brunnett | 600/429 |
| 5,207,223 A | 5/1993 | Adler | |
| 5,411,026 A * | 5/1995 | Carol | 600/439 |
| 5,427,097 A | 6/1995 | Depp | |
| 6,149,592 A * | 11/2000 | Yanof et al. | 600/427 |
| 6,298,110 B1 * | 10/2001 | Ning | 378/4 |
| 6,307,914 B1 | 10/2001 | Kunieda et al. | |
| 6,333,991 B1 * | 12/2001 | Schreiber et al. | 382/132 |
| 6,370,417 B1 * | 4/2002 | Horbaschek et al. | 600/424 |
| 6,501,981 B1 | 12/2002 | Schweikard et al. | |
| 6,542,770 B2 * | 4/2003 | Zylka et al. | 600/424 |
| 6,842,502 B2 * | 1/2005 | Jaffray et al. | 378/65 |
| 6,978,166 B2 * | 12/2005 | Foley et al. | 600/425 |
| 7,050,844 B2 * | 5/2006 | Strobel | 600/424 |
| 7,251,522 B2 * | 7/2007 | Essenreiter et al. | 600/424 |
| 7,327,865 B2 | 2/2008 | Fu et al. | |

(Continued)

FOREIGN PATENT DOCUMENTS

WO   WO2005/024721 A2   3/2005

(Continued)

OTHER PUBLICATIONS

Dongshan Fu et al., "Automated Skull Tracking for the CyberKnife Image-guided Radiosurgery System", Accuray, Inc., 1310 Chesapeake Terrace, Sunnyvale, CA 94089 & Bristol Regional Medical Center, 1 Medical Park Blvd., Bristol, TN 37620. 1994-2004, pp. 12 total.

(Continued)

*Primary Examiner*—Aaron W Carter
(74) *Attorney, Agent, or Firm*—Blakely, Sokoloff, Taylor & Zafman LLP

(57) ABSTRACT

A method for precision registration of X-ray images to cone-beam CT scan for image-guided radiosurgery includes acquiring 2-D pre-treatment X-ray images of a region of interest, acquiring a 2-D X-ray image of the region of interest at approximately a time of treatment, registering the 2-D X-ray image with a corresponding 2-D pre-treatment X-ray image to obtain a 2-D registration result at approximately the time of treatment, and converting the 2-D registration result into a 3-D tracking result to track the region of interest.

36 Claims, 8 Drawing Sheets

U.S. PATENT DOCUMENTS

| | | | |
|---|---|---|---|
| 7,366,562 B2 * | 4/2008 | Dukesherer et al. | 600/424 |
| 2001/0029334 A1 * | 10/2001 | Graumann et al. | 600/437 |
| 2002/0128551 A1 * | 9/2002 | Grass et al. | 600/427 |
| 2003/0014034 A1 * | 1/2003 | Strobel | 604/407 |
| 2004/0114790 A1 * | 6/2004 | Yamamoto et al. | 382/131 |
| 2005/0047544 A1 * | 3/2005 | Fu et al. | 378/63 |
| 2005/0049477 A1 | 3/2005 | Fu et al. | |
| 2005/0049478 A1 | 3/2005 | Kuduvalli et al. | |
| 2005/0251029 A1 * | 11/2005 | Khamene et al. | 600/427 |
| 2005/0256398 A1 * | 11/2005 | Hastings et al. | 600/423 |

FOREIGN PATENT DOCUMENTS

| | | | |
|---|---|---|---|
| WO | WO2005/024721 A3 | 3/2005 | |

OTHER PUBLICATIONS

David Sarrut et al., "Geometrical transformation approximation for 2D/3D intensity-based registration of portal images and CT scan", dsarrut@univ-lyon2.fr, ERIC Laboratory, France, sclippe@univ-lyon2.fr. Centre de Lutte Contre le Cancer Leon Berard, France, 1991-2000, pp. 9 total.

Int'l. PCT Search Report PCT/US06/25120, Mailing date: Sep. 18, 2007 (6 pages).

PCT Written Opinion PCT/US06/25120, Mailing date: Sep. 18, 2007 (6 pages).

Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, 12 pages.

International Search Report and Written Opinion, PCT/US06/25120, International filing date: Jue 27, 2006, date of mailing: Sep. 18, 2007, pp. 12 total.

PCT Int'l. Preliminary Report on Patentability and Written Opinion for PCT /US2006/025120, mailing date Sep. 18, 2007, 6 pages.

PCT International Search Report, PCT/US06/25120, International filing date Jun. 27, 2006, mailed Nov. 14, 2007.

PCT Written Opinion of the International Searching Authority, PCT/US06/25120, International filing date Jun. 27, 2006, mailed Nov. 14, 2007.

International Preliminary Report on Patentability, PCT/US2006/025120, filing date Jun. 27, 2006, mailed Jan. 17, 2008, 6 pages.

Anthony E. Lujan et al., Determination of rotations in three dimensions using two-dimensional portal image registration, Med. Phys. 25 (5), May 1998, pp. 703-708.

First Notification of Office Action, Chinese Patent Application No. 200680028160.0, dated Nov. 20, 2009, 4 pages.

Extended European Search Report, application No. EP06774165 dated Feb. 2, 2010, mailed Feb. 11, 2010.

* cited by examiner

PRECISION REGISTRATION OF X-RAY IMAGES TO CONE-BEAM CT SCAN FOR IMAGE-GUIDED RADIATION TREATMENT

TECHNICAL FIELD

The present invention relates generally to image-guided radiation treatment systems and, in particular, to the registration of pre-treatment X-ray images with X-ray images acquired during treatment delivery.

BACKGROUND

Oncology is the branch of medicine that deals with tumors, including the study of their development, diagnosis, treatment and prevention. A tumor is an abnormal growth of tissue resulting from the uncontrolled, progressive multiplication of cells, serving no physiological function. A tumor may be malignant (cancerous) or benign. A malignant tumor is one that spreads cancerous cells to other parts of the body (metastasizes) through blood vessels or the lymphatic system. A benign tumor does not metastasize, but can still be life-threatening if it impinges on critical body structures such as nerves, blood vessels and organs.

Radiosurgery and radiotherapy are radiation treatment systems that use external radiation beams to treat tumors and other lesions by delivering a prescribed dose of radiation (e.g., X-rays or gamma rays) to a target area (region of interest, or ROI) while minimizing radiation exposure to the surrounding tissue. The object of both radiosurgery and radiotherapy is the destruction of tumorous tissue while sparing healthy tissue and critical structures. Radiotherapy is characterized by a low radiation dose per treatment and many treatments (e.g., 30 to 45 days of treatment). Radiosurgery is characterized by a relatively high radiation dose to a tumor in one, or at most a few, treatments. In both radiotherapy and radiosurgery, the radiation dose is delivered to the tumor site from multiple angles. As the angle of each radiation beam is different, every beam passes through the tumor site, but passes through a different area of healthy tissue on its way to the tumor. As a result, the cumulative radiation dose at the tumor is high and the average radiation dose to healthy tissue is low.

Conventional radiotherapy and radiosurgery treatment systems use a rigid and invasive stereotactic (3-dimensional reference) frame to immobilize a patient during a diagnostic/treatment planning CAT (computed axial tomography) scan or other 3-D imaging modality (e.g., MRI or PET scan) that images the region of interest, and during subsequent radiation treatments. The rigid frame is attached to bony structures in the patient (e.g., the skull) so that reference marks on the frame (fiducials) have a fixed spatial relationship with the region to be imaged (e.g., the brain). Subsequently, during treatment, the frame provides points of reference for the location of a radiation beam (or beams). In a conventional radiosurgery system, a distributed radiation source (e.g., cobalt 60) is used to produce a number of simultaneous radiation beams through holes in a custom-machined radiation shield. In a conventional radiotherapy system, the radiation source is a single beam device mounted in a gantry structure that rotates around the patient in a fixed plane of rotation. Every beam passes through the center of rotation (the isocenter) and the patient must be properly positioned or repositioned with respect to the isocenter before each radiation beam is applied.

Image-guided radiotherapy and radiosurgery systems (together, image-guided radiation treatment, or IGR treatment systems) eliminate the use of invasive frame fixation by correcting for differences in patient position between the treatment planning phase (pre-treatment imaging phase) and the treatment delivery phase (in-treatment phase). This correction is accomplished by acquiring real-time X-ray images during the treatment delivery phase and registering them with reference images, known as digitally reconstructed radiograms (DRRs), rendered from a pre-treatment CAT scan.

FIG. 1 illustrates a schematic representation of a CAT scanner. As shown in FIG. 1, an X-ray source produces a fan beam of X-rays that travels through the patient and impinges on a detector. While the treatment table is stationary, a cross-sectional image of the patient is obtained by rotating the X-ray source and detector around the patient and scanning a transverse slice of the body from different angular positions. After each cross-sectional slice is complete, the table is advanced (perpendicular to the plane of FIG. 1) and the next cross-sectional slice is obtained. A three-dimensional (3-D) image (CT volume) is obtained by integrating the image data from the slices. The CAT scan is used to develop a treatment plan that calculates the angle, duration and intensity of the X-rays beams needed to deliver the prescribed radiation dose.

A DRR is a synthetic X-ray image produced by combining data from the CAT scan slices and computing a two-dimensional (2-D) projection through the slices that approximates the geometry of the real-time imaging system. The registration process between the DRR's and the real-time X-ray images is designed to correct for translational and rotational misalignments between the reference images and the real-time images.

The accuracy of the registration is limited by the accuracy of the DRR's used for the registration process. The accuracy of the DRRs is limited, in turn, by the resolution of the diagnostic CAT scan. As noted above, a DRR is a synthetic X-ray. A DRR is obtained by integrating tracing lines from slice-to-slice through the CT volume. Compared to X-ray images, DRRs are blurred and some image details may be lost. Thus, the registration process compares high-quality real-time X-ray images to low quality DRR images and the overall quality of the registration is limited by the resolution of the DRR.

FIG. 2 illustrates one potential problem associated with the use of DRR's. In FIG. 2, a tumor mass is shown in close proximity to a blood vessel with an irregularity. The CAT scan consists of a series of cross-sectional slices separated by a series of increments, where the increments serve to limit the total X-ray exposure of the patient to safe levels. When a DRR is generated from the CAT scan data, the image is rendered by linear interpolation between the slices, which washes out details in the rendered image. FIG. 3 illustrates such a rendering of the tumor mass and blood vessel from the data obtained from FIG. 2. In FIG. 3, the irregularity in the blood vessel is lost because the increment between the CAT scan slices is greater than the size of the irregularity. The loss of feature data degrades the effectiveness of any similarity measures between the DRR and the real-time X-ray images used to drive the registration process. The DRR rendering process also causes a loss of density variation data in the increments, which may make it difficult or impossible to track the movement of soft tissue structures during treatment.

BRIEF DESCRIPTION OF THE DRAWINGS

The present invention is illustrated by way of example, and not by limitation, in the figures of the accompanying drawings in which.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems. The term "X-Ray image" as used herein may mean a visible X-ray image (e.g., displayed on a video screen) or a digital representation of an X-ray image (e.g., a file corresponding to the pixel output of an X-ray detector). The terms "in-treatment image" or "real-time image" as used herein may refer to images captured at any point in time during a treatment delivery phase of a radiosurgery or radiotherapy procedure, which may include times when the radiation source is either on or off. The term IGR as used herein may refer to image-guided radiotherapy, image-guided radiosurgery or both.

A method and system for the precision registration of x-ray images to CT scan images for image-guided radiosurgery and radiotherapy is described. In one embodiment, the method may include acquiring 2-D pre-treatment X-ray images of a region of interest from a pre-treatment imaging system (e.g., during a treatment planning phase). The method may also include acquiring a 2-D in-treatment X-ray image of the region of interest (e.g., during a treatment delivery phase), and registering the 2-D in-treatment X-ray image with a corresponding 2-D pre-treatment X-ray image to obtain a 2-D registration result. Finally, the method may include converting the 2-D registration result into a 3-D tracking result to track the region of interest during an image-guided radiosurgery or radiotherapy (IGR) procedure.

Figure 1:
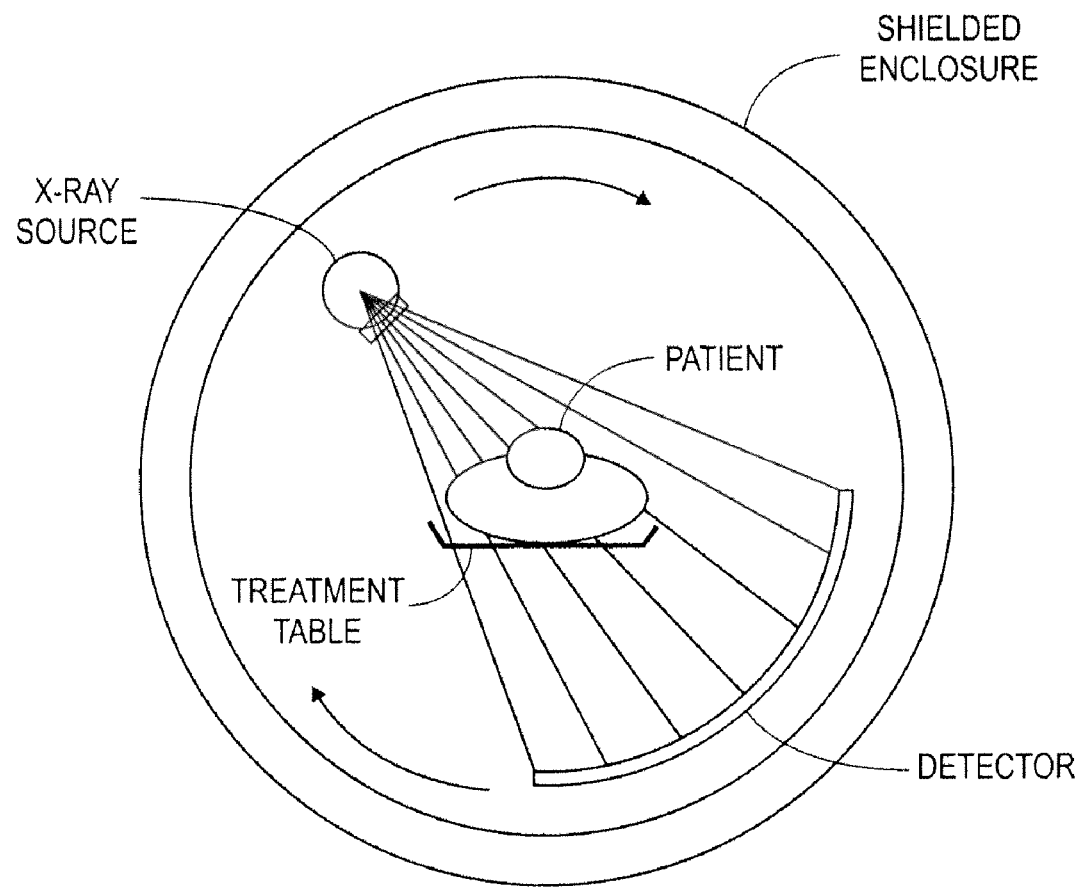
FIG. 1 illustrates a conventional CAT scan apparatus.
Figure 2:
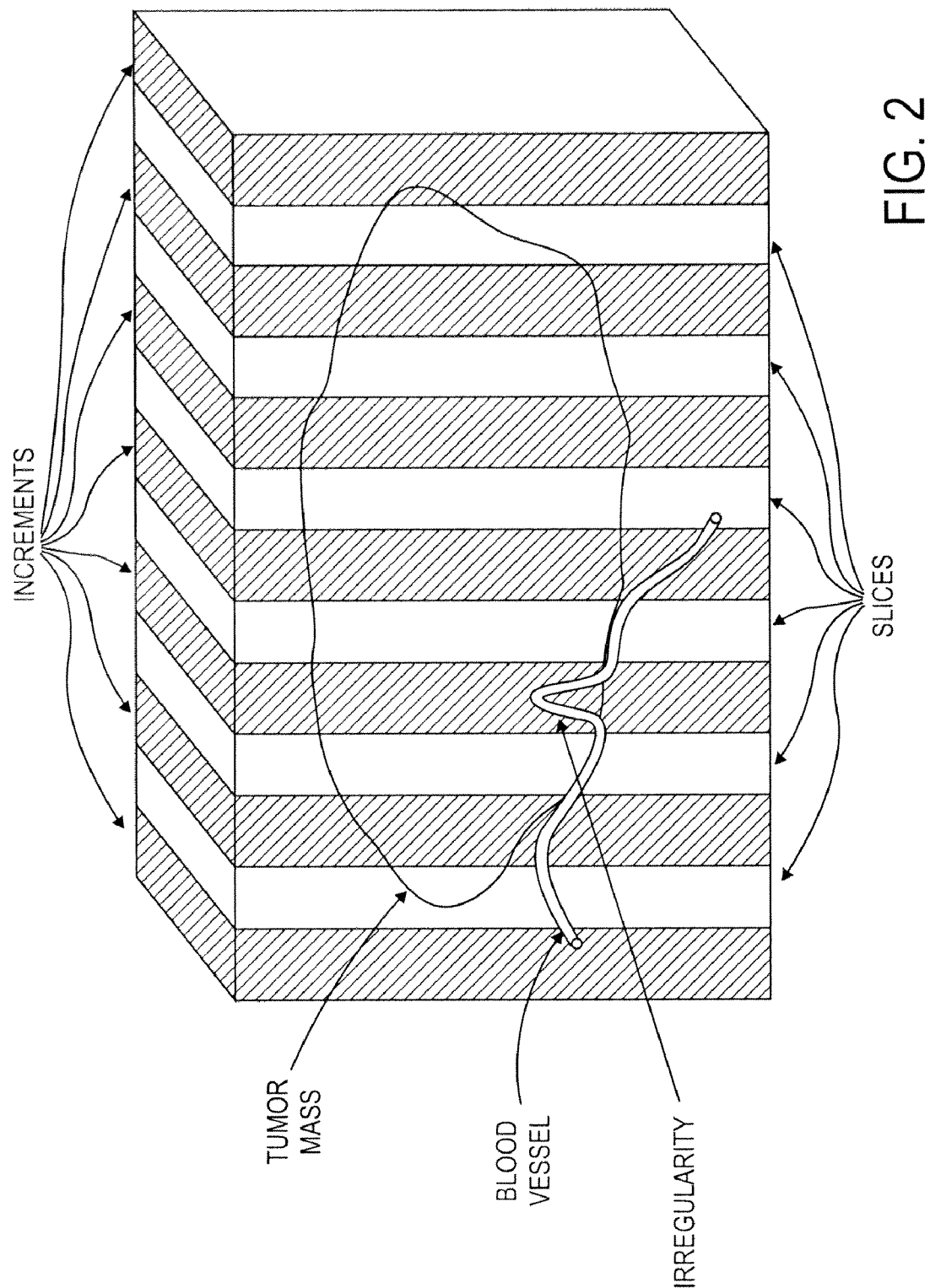
FIG. 2 illustrates cross-sectional imaging in a conventional CAT scan system.
Figure 3:
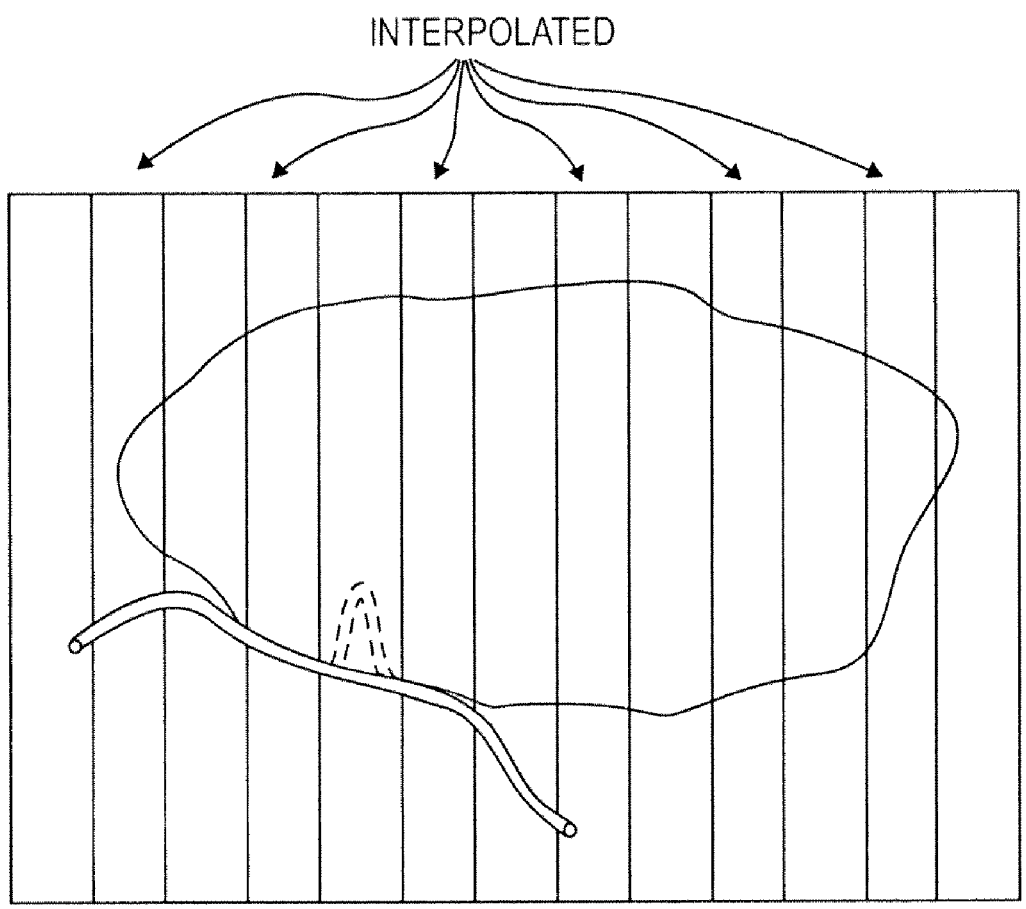
FIG. 3 illustrates DRR rendering in a conventional CAT scan system.
Figure 4:
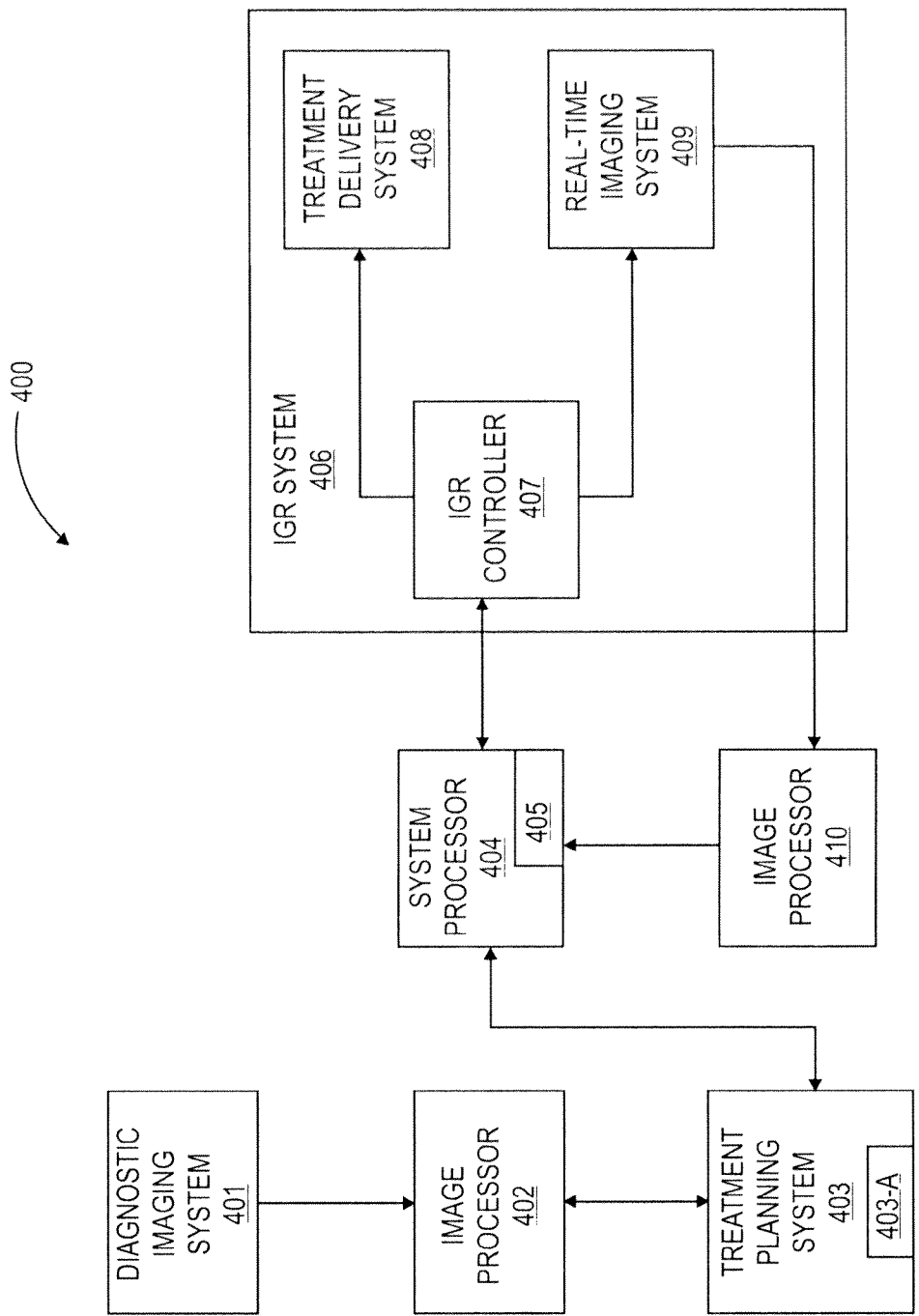
FIG. 4 illustrates a system in one embodiment of precision registration of x-ray images to cone-beam CT scan for image-guided radiation treatment.

In one embodiment, illustrated in FIG. 4, a treatment planning and delivery system 400 includes a diagnostic imaging system 401 to acquire pre-treatment X-ray images of a region of interest in a patient. Diagnostic imaging system 401 may be an imaging system that produces high-quality 2-D X-ray images directly, as part of a 3-D imaging and diagnostic process. For example, diagnostic imaging system 401 may be a cone-beam CT scanner that produces a set of projected 2-D X-ray images by rotating one or more pairs of X-ray sources and detectors around a patient. Cone-beam CT scanners are known in the art and, accordingly, will not be described in detail herein. Alternatively, diagnostic imaging system 401 may be any other imaging system that produces 2-D X-ray images directly without intermediate transformations. The X-ray images produced by diagnostic imaging system 401 may include pairs of orthogonal projections through a region of interest in a patient, generated sequentially by a single source and detector or simultaneously by two sets of sources and detectors. The set of images acquired by diagnostic imaging system 401 may include a sufficient number of images of the region of interest to construct a CT volume for diagnosis and treatment planning. Alternatively, the set of pre-treatment 2-D X-ray images acquired by diagnostic imaging system 401 may be a smaller number of images corresponding approximately to an expected range of 2-D in-treatment X-ray images of the region of interest during the image-guided radiation treatment procedure, in which case the set of pre-treatment X-ray images may be correlated with a conventional CAT scan. The expected range of 2-D in-treatment X-ray images may correspond to an expected range of patient positions during the IGR procedure, which positions may deviate from the position or positions of the patient during the pre-treatment image acquisition process.

Images acquired by diagnostic imaging system 401 may be processed to enhance image features by image processor 402, using digital enhancement techniques known in the art, and may be stored in a treatment planning library 403-A within treatment planning system 403. Treatment planning library 403-A may be any kind of digital storage medium such as, for example, magnetic or solid state media capable of storing digital X-ray images. Treatment planning system 403 may be configured to render 3-D diagnostic images and one or more treatment plans, which treatment plans may include the spatial relationship between a radiation treatment X-ray source and the region of interest during a prospective IGR procedure. Treatment planning system 403 may be coupled to a system processor 404 which may be any type of general purpose or special purpose processing device capable of executing instructions and operating on image data and other data, and of commanding an IGR system, such as IGR system 406. System processor 404 may include a memory 405, which may be any type of memory capable of storing data and instructions for operating system 400. In one embodiment, IGR system 406 may be a frameless robot-based linear accelerator (LINAC) radiosurgery system, for example, a CyberKnife® Stereotactic Radiosurgery System manufactured by Accuray, Inc. of Sunnyvale Calif. IGR system 406 may include an IGR controller 407 coupled with an IGR delivery system 408 and a real-time imaging system 409. IGR controller 407 may be configured to coordinate the operations of IGR delivery system 408 and real-time imaging system 409 in response to commands from system processor 404. Real-time X-ray images acquired from real-time imaging system 409 may be processed by image processor 410 to enhance image features, as noted above, which may improve similarity measures between the pre-treatment and in-treatment images. Registration of the pre-treatment and in-treatment images may be performed by system processor 404 on image data sent to system processor 404 from treatment planning system 403 and real-time imaging system 409. The registration of the pre-treatment and in-treatment X-ray images may include calculation of in-plane translations, in-plane rotation and out-of-plane rotation, as is known in the art.

Figure 5:
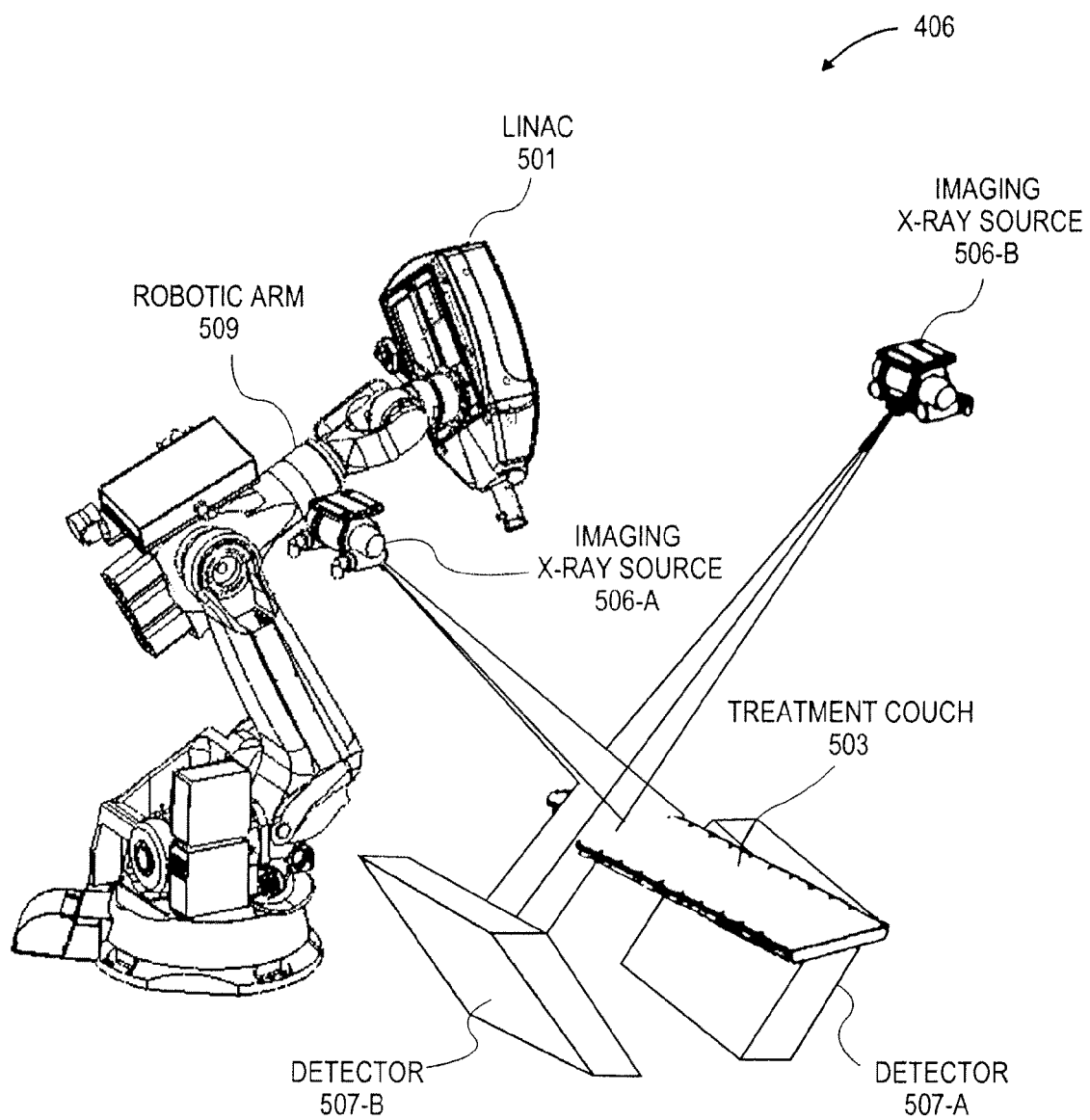
FIG. 5 illustrates one embodiment of an image-guided radiation treatment system.

FIG. 5 illustrates one embodiment of a frameless robot-based LINAC radiosurgery system that may be used with the present invention. In FIG. 5, treatment delivery system 408 may include a linear accelerator (LINAC) 501 to generate radiosurgery X-ray beams, a robotic arm 509 to position LINAC 501 to a patient and the region of interest, and a treatment table 503 to position a patient with respect to real-time imaging system 409. In such a system, the LINAC 501 is mounted on the end of a robotic arm 509 to provide multiple (e.g., 5 or more) degrees of freedom of motion in order to position the LINAC to irradiate tumorous tissue with highly-collimated beams delivered from many angles in an operating volume (e.g., sphere) around the patient. Treatment may involve beam paths with a single isocenter, multiple isocenters, or with a non-isocentric approach (e.g., the beams need only intersect with the targeted tumor mass and do not necessarily converge on a single point, or isocenter, within the target region). Treatment can be delivered in either a single session (mono-fraction) or in a small number of sessions (hypo-fractionation) as determined during treatment planning.

Alternatively, other types of treatment delivery systems may be used. One example is gantry-based (isocentric) intensity modulated radiotherapy (IMRT) systems. In a gantry-based system, a radiation source (e.g., a LINAC) is mounted on a rotating gantry such that it rotates in a fixed plane corresponding to an axial slice of the patient. Radiation is then delivered from several angular positions in the plane of rotation. In IMRT, the shape of the radiation beam is defined by a multi-leaf collimator that allows portions of the beam to be blocked, so that the remaining beam incident on the patient has a pre-defined shape. In IMRT planning, the treatment planning algorithm selects subsets of the main beam and determines the amount of exposure time for each subsidiary beam to meet the overall radiation dose constraints. Other examples of treatment delivery systems include gamma ray delivery systems (e.g., using a cobalt isotope as a radiation source).

IGR controller 407 (not shown in FIG. 5) may be imbedded in robotic arm 509 or may be a separate component. In FIG. 5, real-time imaging system 409 may include imaging X-ray sources 506-A and 506-B and X-ray image detectors 507-A and 507-B. The X-ray image detectors 507-A and 507-B may be amorphous silicon detectors, capable of producing high-quality 2-D X-ray images during an IGR procedure, and may be mounted at 90 degrees relative to one another and at 45 degrees to the floor. During the treatment phase, the patient may be imaged at 45 degree LAO (left anterior oblique) and RAO (right anterior oblique) angles to facilitate reconstructing the 2D images into 3D space as described below. Other embodiments of IGR system 406 may include gantry based radiotherapy or radiosurgery systems as are known in the art.

Figure 6:
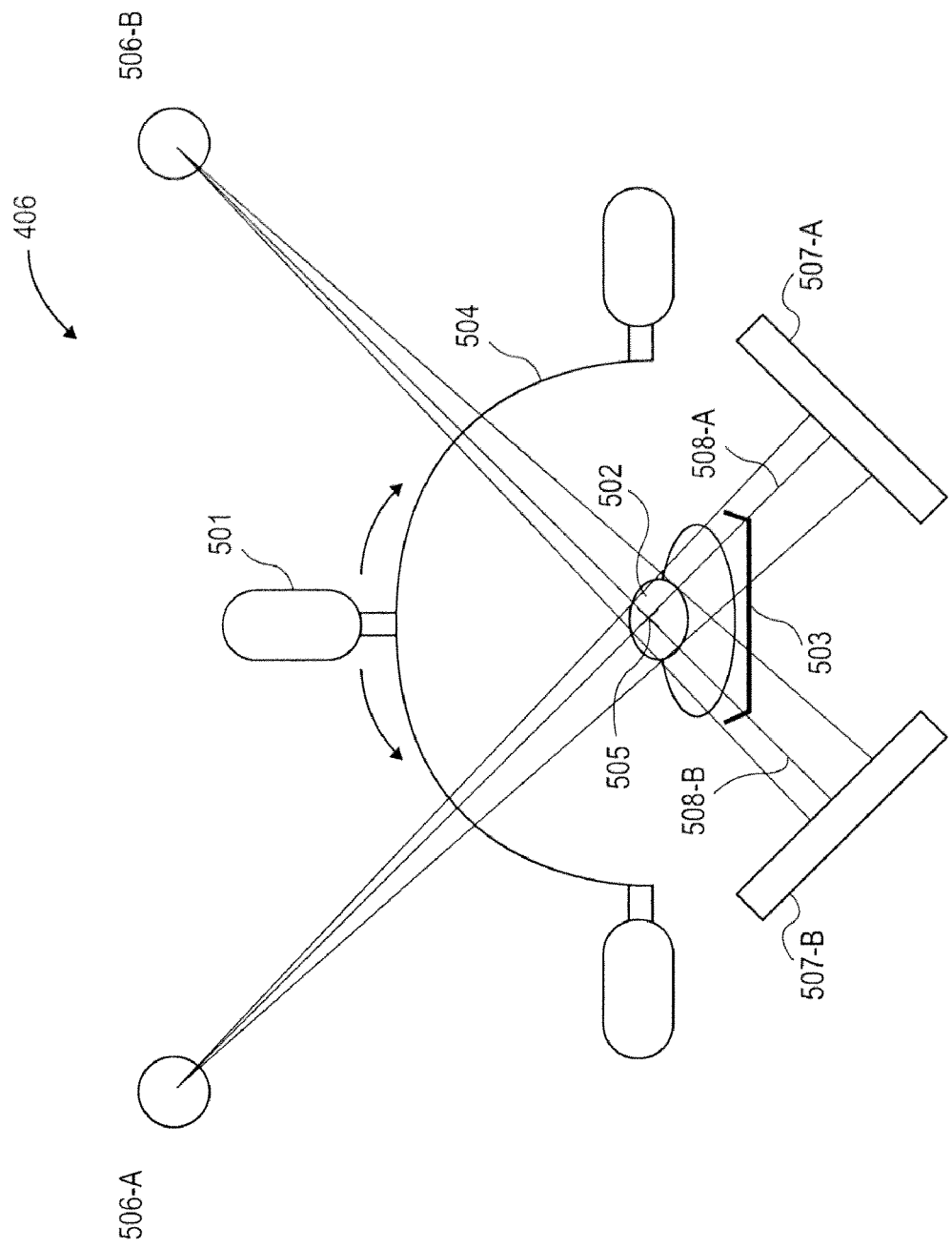
FIG. 6 illustrates one embodiment of an imaging system.

FIG. 6 illustrates the exemplary IGR system 406 of FIG. 5 in schematic form. In FIG. 6, robotic arm 509 is omitted for clarity. As shown in FIG. 6, LINAC 501 may be positioned to deliver high-energy radiation to a region of interest in patient 502. Motorized treatment couch 503 may be used to position the region of interest in patient 502 with respect to a machine center 505, described in greater detail below. As noted above, robotic arm 509 may provide six-degrees of freedom (e.g., three Cartesian coordinates plus rotations around each coordinate) in positioning LINAC 501. LINAC 501 may be positioned at any point in an approximately hemispherical area 504 surrounding machine center 505. Imaging X-ray sources 506-A and 506-B may be mounted outside of the range of motion of the LINAC 501 and aligned to illuminate two orthogonally positioned X-ray detectors 507-A and 507-B. X-ray beams from sources 506-A and 506-B may be used to define machine center 505, indicated by the "x" in FIG. 6, at the crossing point of traced rays 508-A and 508-B from the X-ray sources 506-A and 506-B, respectively, which are normal to their respective detectors 507-A and 507-B. Machine center 505 may be used as a reference point for the registration of pre-treatment X-ray images with in-treatment X-ray images. It should be noted that alternative imaging configurations and geometries may be employed. For example, the angle between X-ray detectors 507-A and 507-B may be more or less than 90 degrees. In other embodiments, additional X-ray sources and detectors may be employed to define one or more additional machine centers.

Figure 7:
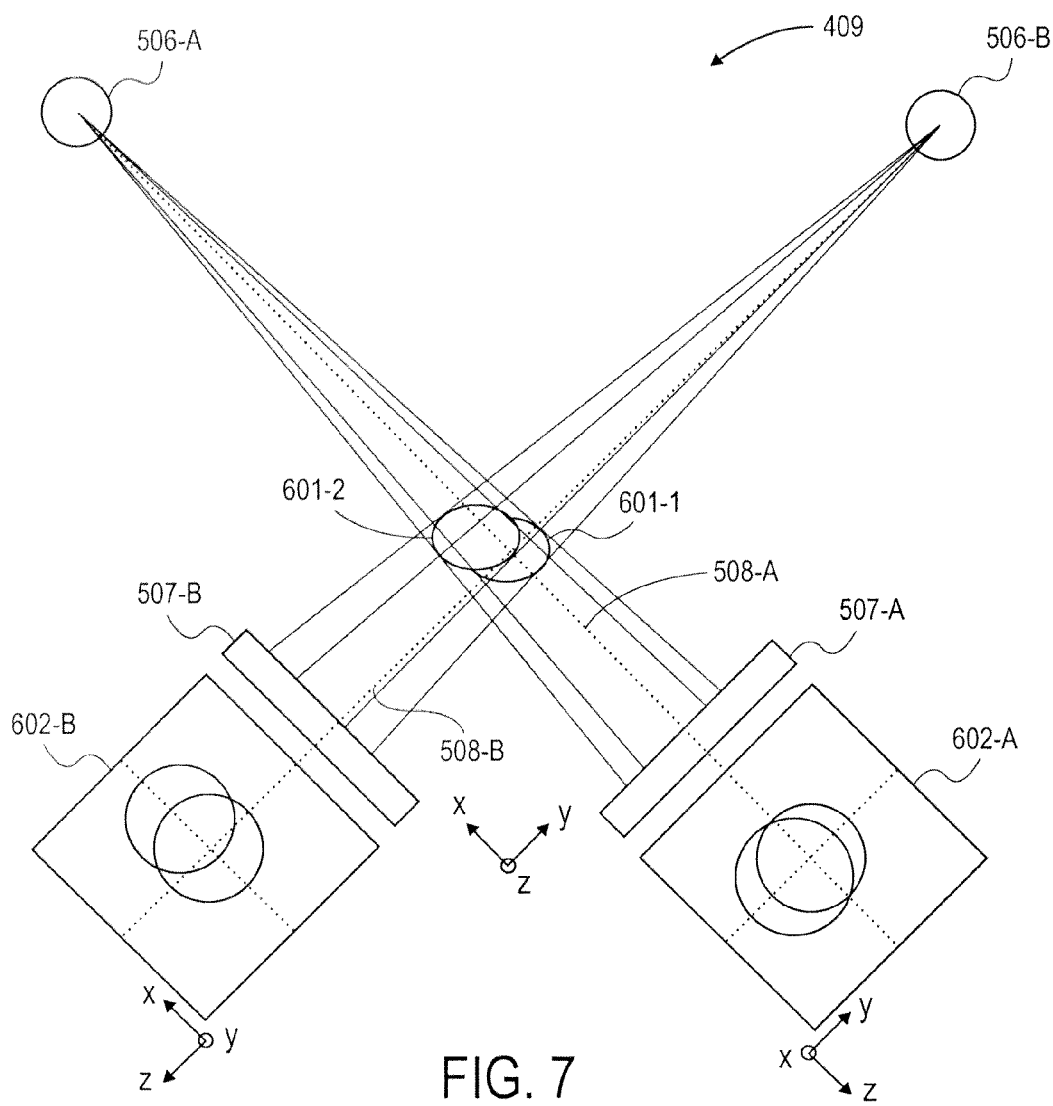
FIG. 7 illustrates a real-time imaging system in one embodiment of precision registration of x-ray images to cone-beam CT scan for image-guided radiation treatment.

FIG. 7 illustrates how patient movement may be detected with real-time imaging system 409 during an IGR procedure. In FIG. 7, the projected images of the patient in two positions 601-1 and 601-2 are shown in projections 602-A and 602-B, referenced to the (x,y,z) coordinate system of the imaging system, where a circle indicates a coordinate direction into the plane of the figure. Projection 602-A detects motions in the Y-Z plane while projection 602-B detects motion in the X-Z plane. Such an orthogonal projection system is known in the art and, accordingly, will not be described in detail herein. The combination of projection 602-A and 602-B may provide positional information in all three coordinate axes which may be communicated to IGR controller 407 by way of system processor 405 to locate patient 502 with respect to machine center 505.

During the treatment delivery phase, 2-D real-time X-ray images of the patient may be acquired by real-time imaging system 409 every time before the LINAC is to be repositioned and activated. The in-treatment X-ray images may be compared with the set of high-quality 2-D pre-treatment X-ray images maintained in treatment planning library 402, and the closest matches may be selected for registration. A direct comparison of the real-time X-ray images with the pre-treatment images may not achieve an exact match because: 1) the geometry of the pre-treatment imaging system may be different from the geometry of the real-time imaging system (e.g., the distances from source to region of interest and from region of interest to detector may be different in the two imaging systems) resulting in different image sizes, and 2) the patient is not a rigid body and is capable of rotational displacements about each axis (yaw, pitch and roll), and bodily compressions or extensions at the time of treatment, relative to pre-treatment positioning. Thus, the pre-treatment images may require registration with the in-treatment images to insure that the radiation treatment is delivered to the region of interest (e.g., tumor mass) in accordance with the treatment plan.

In one embodiment, before each beam activation, the two orthogonally projected real-time X-ray images are compared and registered with two closely corresponding orthogonally projected pre-treatment X-ray images. The 2-D registration in each projection may be carried out independently, correcting for in-plane translations and rotations (e.g., Y-Z translations and rotations in projection 602-A and X-Z translations and rotations in projection 602-B) and the results are combined and converted to a 3-D rigid transformation that provides a 3-D tracking result that is used to correct the position of LINAC 501 prior to the delivery of a radiation dose. The 3-D transformation provides estimates of the in-plane translational and out-of-plane rotational differences between the real-time images and the reference images using similarity measures based, for example, on image features (such as anatomical edges, image gradients, contours, object surfaces or segmented objects) or image intensity. Image registration techniques are known in the art, for example, as described in Published U.S. Patent Applications 2005/0047544, 2005/0049477 and 2005/0049478. In embodiments of the present invention, the availability of high-quality pre-treatment X-ray images improves feature extraction and soft tissue visualization compared to synthetic DRR images and allows the registration error to be driven to approximately zero by minimization techniques employed in the registration process that are known in the art.

In another embodiment, the 3-D treatment plan may be developed with a different modality (e.g., a conventional CT scan) and the 2-D pre-treatment images may be separately correlated with the 3-D treatment plan.

In yet another embodiment, where the imaging geometries of the pre-treatment imaging system and the in-treatment imaging system are different, the in-treatment image may be scaled (e.g., by a scaling algorithm in the system processor) to correct for the different geometries.

Figure 8:
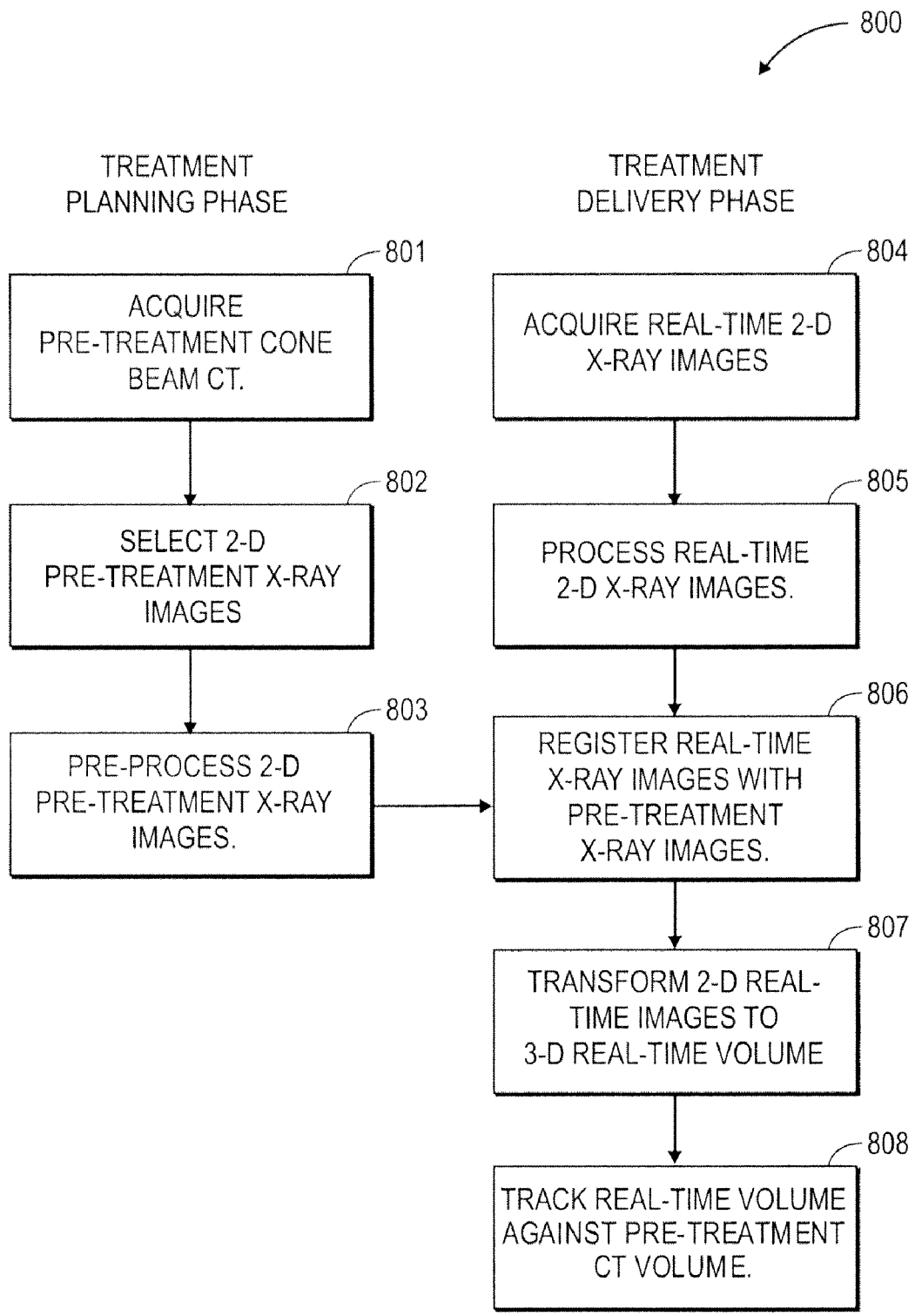
FIG. 8 illustrates a method in one embodiment of precision registration of x-ray images to cone-beam CT scan for image-guided radiation treatment.

FIG. 8 illustrates a method 800 in one embodiment of precision registration of X-ray images to CT scan for image-guided radiosurgery and radiotherapy. With reference to FIG. 4, the method may include, in a treatment planning phase: acquiring a cone beam CT scan volume with a diagnostic imaging system 401 (step 801); selecting 2-D pre-treatment X-ray images from the cone beam CT with a treatment planning system 402 (step 802); and pre-processing the 2-D pre-treatment X-ray images with image processor 403 to extract pre-treatment X-ray image features (step 803). In a treatment delivery phase, the method may include: acquiring 2-D real-time X-ray images with a real-time imaging system 409 (step 804); processing the 2-D real-time X-ray image with image processor 410 to extract real-time X-ray image features and to optionally scale the 2-D real-time X-ray image to correct for different imaging geometries between the diagnostic imaging system 401 and the real-time imaging system 409 (step 805); registering the 2-D real-time X-ray images with corresponding 2-D pre-treatment X-ray images in system processor 404 to obtain a 2-D registration result (step 806); performing a geometric transformation, in system processor 404, to convert the 2-D real-time X-ray images to a 3-D real-time volume (step 807); and tracking the 3-D real-time volume against the pre-treatment CT volume (step 808).

Thus, a system and method for precision registration of X-ray images to CT scan for image-guided radiosurgery has been described. It will be apparent from the foregoing description that aspects of the present invention may be embodied, at least in part, in software. That is, the techniques may be carried out in a computer system or other data processing system in response to its processor, such as system processor 404, executing sequences of instructions contained in a memory, such as memory 405. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as system processor 404 or IGR controller 407.

A machine-readable medium can be used to store software and data which when executed by a data processing system causes the system to perform various methods of the present invention. This executable software and data may be stored in various places including, for example, memory 405 and treatment planning library 403-A or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method, comprising:
acquiring two-dimensional (2-D) X-ray images of a region of interest at approximately a time of treatment, wherein the 2-D X-ray images comprise a first pair of projected images of the region of interest; and
registering the 2-D X-ray images with corresponding 2-D pre-treatment X-ray images, comprising a second pair of projected images of the region of interest, to obtain a 2-D registration result at approximately the time of treatment.

2. The method of claim 1, further comprising converting the 2-D registration result into a 3-D tracking result to track the region of interest at approximately the time of treatment.

3. The method of claim 1, wherein the 2-D pre-treatment X-ray images correspond to an expected range of 2-D X-ray images of the region of interest at approximately the time of treatment.

4. The method of claim 3, wherein the expected range of 2-D X-ray images corresponds to an expected range of patient positions at approximately the time of treatment.

5. The method of claim 1, wherein the 2-D pre-treatment X-ray images comprise a first plurality of paired orthogonal projections of the region of interest and wherein the 2-D X-ray images comprise a second plurality of paired orthogonal projections of the region of interest at approximately the time of treatment.

6. The method of claim 1, wherein registering the 2-D X-ray images with the corresponding 2-D pre-treatment X-ray images at approximately the time of treatment comprises calculating an in-plane translation, an in-plane rotation and an out-of-plane rotation.

7. The method of claim 1, wherein the 2-D pre-treatment X-ray images comprise a subset of a cone-beam CT scan used for 3-D treatment planning.

8. The method of claim 1, further comprising developing a 3-D treatment plan with a CAT scan.

9. The method of claim 1, wherein the 2-D pre-treatment X-ray images and the 2-D X-ray images correspond to different imaging geometries, further comprising scaling the 2-D X-ray images at approximately the time of treatment to correct for the different imaging geometries.

10. The method of claim 1, further comprising processing the 2-D pre-treatment X-ray images to extract image features for registration with the 2-D X-ray images at approximately the time of treatment.

11. A non-transitory computer-readable storage medium containing instructions that when executed on a data processing system causes the system to perform operations, comprising:
    acquiring two-dimensional (2-D) X-ray images of a region of interest at approximately a time of treatment, wherein the 2-D X-ray images comprise a first pair of projected images of the region of interest; and
    registering the 2-D X-ray images with corresponding 2-D pre-treatment X-ray images, comprising a second pair of projected images of the region of interest, to obtain a 2-D registration result at approximately the time of treatment.

12. The computer-readable storage medium of claim 11, the operations further comprising converting the 2-D registration result into a 3-D tracking result to track the region of interest at approximately the time of treatment.

13. The computer-readable storage medium of claim 11, wherein the 2-D pre-treatment X-ray images correspond to an expected range of 2-D X-ray images of the region of interest at approximately the time of treatment.

14. The computer-readable storage medium of claim 13, wherein the expected range of 2-D X-ray images corresponds to an expected range of patient positions at approximately the time of treatment.

15. The computer-readable storage medium of claim 11, wherein the 2-D pre-treatment X-ray images comprise a first plurality of paired orthogonal projections of the region of interest and wherein the 2-D X-ray images comprise a second plurality of paired orthogonal projections of the region of interest at approximately the time of treatment.

16. The computer-readable storage medium of claim 11, wherein registering the 2-D X-ray images with the corresponding 2-D pre-treatment X-ray images at approximately the time of treatment comprises calculating an in-plane translation, an in-plane rotation and an out-of-plane rotation.

17. The computer-readable storage medium of claim 11, wherein the 2-D pre-treatment X-ray images comprise a subset of a cone-beam CT scan used for 3-D treatment planning.

18. The computer-readable storage medium of claim 11, wherein the plurality of 2-D pre-treatment X-ray images and the 2-D X-ray images correspond to different imaging geometries, the method further comprising scaling the 2-D X-ray image at approximately the time of treatment to correct for the different imaging geometries.

19. The computer-readable storage medium of claim 11, the operations further comprising processing the 2-D pre-treatment X-ray images to extract image features for registration with the 2-D X-ray images at approximately the time of treatment.

20. An apparatus, comprising:
    an imaging system to acquire 2-D X-ray images of a region of interest at approximately a time of treatment, wherein the 2-D X-ray images comprise a first pair of projected images of the region of interest;
    a processing device coupled with the imaging system to control the imaging system, to register the 2-D X-ray images with corresponding 2-D pre-treatment X-ray images, comprising a second pair of projected images of the region of interest, and obtain a 2-D registration result at approximately the time of treatment.

21. The apparatus of claim 20, the processing device to convert the 2-D registration result into a 3-D tracking result to track the region of interest at approximately the time of treatment.

22. The apparatus of claim 20, wherein the 2-D pre-treatment X-ray images correspond to an expected range of the 2-D X-ray images of the region of interest at approximately the time of treatment.

23. The apparatus of claim 22, wherein the expected range of the 2-D X-ray images corresponds to an expected range of patient positions at approximately the time of treatment.

24. The apparatus of claim 20, wherein the 2-D pre-treatment X-ray images comprise a first plurality of paired orthogonal projections of the region of interest, the imaging system configured to acquire the 2-D X-ray images as a second plurality of paired orthogonal projections of the region of interest at approximately the time of treatment.

25. The apparatus of claim 20, the processing device to register the 2-D X-ray images with the corresponding 2-D pre-treatment X-ray images at approximately the time of treatment by calculating an in-plane translation, an in-plane rotation and an out-of-plane rotation.

26. The apparatus of claim 20, wherein the 2-D pre-treatment X-ray images comprise a subset of a cone-beam CT scan used for 3-D treatment planning, the processing device to convert the 2-D registration result into a 3-D tracking result.

27. The apparatus of claim 20, wherein the 2-D pre-treatment X-ray images and the 2-D X-ray images correspond to different imaging geometries, further comprising a first image processor coupled with the imaging system and the processing device, to scale the 2-D X-ray images at approximately the time of treatment to correct for the different imaging geometries.

28. The apparatus of claim 27, further comprising a second image processor to process the 2-D pre-treatment X-ray images to extract image features for registration with the 2-D X-ray images at approximately the time of treatment.

29. The apparatus of claim 20, further comprising:
    a treatment delivery system to deliver a treatment plan; and
    a controller coupled with the treatment delivery system, the imaging system and the processing device, the controller to coordinate the treatment delivery system with the 3-D tracking result.

30. An image-guided 3-D treatment delivery system, comprising:
    means for acquiring two-dimensional (2-D) X-ray images of a region of interest at approximately a time of treatment, wherein the 2-D X-ray images comprise a first pair of projected images of the region of interest; and
    means for registering the 2-D X-ray images with corresponding 2-D pre-treatment X-ray images, comprising a second pair of projected images of the region of interest, to obtain a 2-D registration result at approximately the time of treatment.

31. The image-guided treatment delivery system of claim 30, further comprising means for converting the 2-D registration result into a 3-D tracking result to track the region of interest at approximately the time of treatment.

32. The image-guided treatment delivery system of claim 30, further comprising means for developing a 3-D treatment plan with a CAT scan.

33. A method, comprising:
    receiving two-dimensional (2-D) pre-treatment X-ray images from a first imaging system that produces the 2-D pre-treatment X-ray images directly without intermediate transformations, wherein the 2-D pre-treatment X-ray images comprise a first pair of projected images of a region of interest; and receiving 2-D in-treatment X-ray images of a region of interest, acquired at approximately a time of treatment, from a second imaging system, wherein the 2-D in-treatment X-ray images comprise a second pair of projected images of the region of interest; and registering the 2-D in-treatment X-ray images with the corresponding 2-D pre-treatment X-ray images to obtain a 2-D registration result at approximately the time of treatment.

34. The method of claim 33, wherein the first imaging system is a cone-beam computed tomography (CT) scanner, and wherein the cone-beam CT scanner produces the 2-D X-ray images by rotating one or more pairs of X-ray sources and detectors around a patient, and wherein the method further comprises:

receiving a cone beam CT scan volume acquired by the cone-beam CT scanner;

selecting the 2-D pre-treatment X-ray images from the cone beam CT scan volume;

pre-processing the 2-D pre-treatment X-ray images to extract pre-treatment X-ray image features; and processing the 2-D in-treatment X-ray images to extract in-treatment X-ray features.

35. The method of claim 34, further comprises scaling the 2-D in-treatment X-ray images to correct for different imaging geometries, if any, between the first imaging system and the second imaging system.

36. The method of claim 34, further comprises:

performing a geometric transformation to convert the 2-D in-treatment X-ray images to a 3-D in-treatment volume; and tracking the 3-D in-treatment volume against the cone beam CT scan volume.

* * * * *